(12) United States Patent
Kitaoka et al.

(10) Patent No.: US 8,173,399 B2
(45) Date of Patent: May 8, 2012

(54) METHOD FOR PRODUCING LACTO-N-BIOSE I AND GALACTO-N-BIOSE

(75) Inventors: Motomitsu Kitaoka, Ibaraki (JP); Mamoru Nishimoto, Ibaraki (JP)

(73) Assignee: Incorporated Administrative Agency National Agriculture and Food Research Organization, Tsukuba-shi (JP)

( * ) Notice: Subject to any disclaimer, the term of this patent is extended or adjusted under 35 U.S.C. 154(b) by 327 days.

(21) Appl. No.: 12/520,668

(22) PCT Filed: Dec. 12, 2007

(86) PCT No.: PCT/JP2007/074362
§ 371 (c)(1),
(2), (4) Date: Jun. 22, 2009

(87) PCT Pub. No.: WO2008/078614
PCT Pub. Date: Jul. 3, 2008

(65) Prior Publication Data
US 2010/0120096 A1    May 13, 2010

(30) Foreign Application Priority Data
Dec. 22, 2006   (JP) ................. 2006-346470

(51) Int. Cl.
*C12P 19/00*   (2006.01)
(52) U.S. Cl. .......... 435/72; 435/193; 435/195; 435/200; 435/233
(58) Field of Classification Search ............. 435/72, 435/193, 195, 200, 233
See application file for complete search history.

(56) References Cited

OTHER PUBLICATIONS

Vetere et al. Eur. J. Biochem. (2000) 267: 942-949.*
Hedbys et al. Glycoconjugate J (1989) 6: 161-168.*
Fan et al. J. Ferment. Bioeng. (1991) 72(2); 92-95.*
Nishimoto et al. Biosci. Biotechnol. Biochem. (2007; published online Aug. 7, 2011) 71(8): 2101-2104.*
Farkas, Erzsebet et al., "Enzymatic Synthesis of Galβ1→3G1cNAc Derivatives Utilising a Phosphorylase from *Bifidobacterium bifidum* 20082", Synlett, Letter, No. 5, pp. 728-730, (2000).
Kitaoka, Motomitsu et al., "Novel Putative Galactose Operon Involving Lacto-N-Biose Phosphorylase in *Bifidobacterium longum*", Applied and Environmental Microbiology, vol. 71, No. 6, pp. 3158-3162, (2005).
Nogi, Yasuhisa "GAL3 Gene Product Is Required for Maintenance of the Induced State of the GAL Cluster Genes in *Saccharomyces cerevisiae*", Journal of Bacteriology, vol. 165, No. 1, pp. 101-106, (1986).
Levander, Fredrik et al., "Enhanced Exopolysaccharide Production by Metabolic Engineering of *Streptococcus thermophilus*", Applied and Environmental Microbiology, vol. 68, No. 2, pp. 784-790, (2002).
Svensson, Malin et al., "Metabolically Improved Exopolysaccharide Production by *Streptococcus thermophilus* and its Influence on the Rheological Properties of Fermented Milk", Applied and Environmental Mircrobiology, vol. 71, No. 10, pp. 6398-6400, (2005).
Office Action issued Dec. 28, 2011 in Korea, patent application No. 10-2009-7013460 with English translation.
News from International Union of Biochemistry and Molecular Biology, "UDP-glucose, UDP-galactose and UDP-glucuronate Biosynthesis, IUBMB 2002", Congress IUBMB & FEBS, Sevilla 2012, Sep. 4-9.
GenBank: AE014295.3, Bifidobacterium Longum NCC2705, Complete Genome (Jan. 2, 2005).

* cited by examiner

*Primary Examiner* — Susan Hanley
(74) *Attorney, Agent, or Firm* — Oblon, Spivak, McClelland, Maier & Neustadt, L.L.P.

(57) ABSTRACT

A method for producing lacto-N-biose I and galacto-N-biose inexpensively and conveniently is provided.
The method for producing lacto-N-biose I or galacto-N-biose, characterized in that the method comprises causing:
(i) a combination of a carbohydrate raw material with an enzyme that catalyzes phosphorolysis of the carbohydrate raw material to give α-glucose-1-phosphate; and
(ii) a combination of an enzyme that converts α-glucose-1-phosphate to UDP-glucose and an enzyme that converts UDP-galactose to galactose-1-phosphate with their cofactors, and/or a combination of an enzyme (UDP-Gly synthase) that converts α-glucose-1-phosphate and UDP-galactose to UDP-glucose and α-galactose-1-phosphate, respectively, with its cofactor(s)
to act in the presence of N-acetylglucosamine or N-acetylgalactosamine, phosphoric acid, lacto-N-biose phosphorylase (EC 2.4.1.211), and UDP-glucose-4-epimerase (EC 5.1.3.2).

8 Claims, 3 Drawing Sheets

Fig. 1

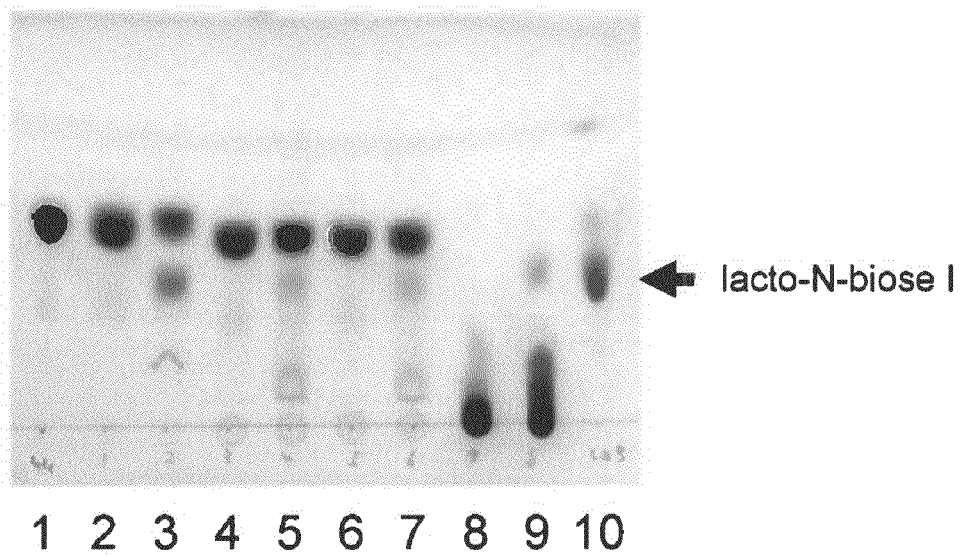

1 glucose
2 sucrose + sucrose phosphorylase blank
3 sucrose + sucrose phosphorylase reaction for 90 hours
4 cellobiose + cellobiose phosphorylase blank
5 cellobiose + cellobiose phosphorylase reaction for 90 hours
6 laminaribiose + laminaribiose phosphorylase blank
7 laminaribiose + laminaribiose phosphorylase reaction for 90 hours
8 maltoheptaose + phosphorylase blank
9 maltoheptaose + phosphorylase reaction for 90 hours
10 lacto-N-biose I

SEQUENCE LISTING

```
<160> NUMBER OF SEQ ID NOS: 20

<210> SEQ ID NO 1
<211> LENGTH: 1820
<212> TYPE: DNA
<213> ORGANISM: Bifidobacterium longum

<400> SEQUENCE: 1
```

```
ggttcgatac atacgtgagt atgcaaatac gtaaacaaca acaggcaga tgcgcacgca      60 aattgcaccc gcgcccatga gccaagggag gtcccatgaa aaacaaagtg caactcatca     120
catacgccga tcgtctcggc gatggcactc ttagctcgat gaccgacatc ctgcgcaccc     180
gcttcgacgg cgtgtatgac ggcgtgcata tcctgccgtt cttcactccg ttcgatggtg     240
cggatgcagg cttcgacccg atcgaccata ccaaagtcga cgaacgtctc ggcagctggg     300
acgacgtcgc cgaactctcc aagacccaca acatcatggt cgacgccatc gtcaaccaca     360
tgagttggga atccaagcag ttccaagacg tgcttgaaaa aggtgaggaa tccgagtatt     420
acccgatgtt cctgaccatg agctccgtct cccgaacgg cgccaccgaa gaagacctgg      480
ccggcatcta ccgcccgcgc cgggcctgc cgttcaccca ctacaagttc gccagcaaga      540
cgcgcttggt ctgggtgagc ttcacccccgc agcaggtgga catcgacact gattccgcca    600
agggttggga atacctgatg tcgatcttcg atcagatggc cgccagccac gtgcgctaca    660
tccgtctcga cgccgtgggc tacggcgcca aggaagccgg caccagctgc ttcatgaccc    720
ccaagacctt taagctcatc tcccgtctgc gcgaggaggg cgtcaagcgc ggccttgaaa    780
tcctcatcga ggttcacagc tactacaaga agcaggtgga aatcgcctcc aaggtggacc    840
gcgtctacga tttcgccctg ccgccgctgc ttctgcactc gctgttcacc ggtcacgtcg    900
aacccgtggc ccactggacc gagatccgcc cgaacaacgc cgtcaccgtg ctcgatacgc    960
acgatggcat cggcgtgatc gacatcggct ccgaccagct cgaccgctcc ctcaagggcc   1020
tcgtgcccga cgaggacgtc gacaacctgg tcaacaccat ccatgccaac acccacggcg   1080
aatcccaggc cgccaccggt gccgccgcgt ccaacctcga cctctaccag gtcgactcca   1140
cgtactactc ggccctcggc tgcaacgacc agcactactt ggccgcccgc gccgtgcagt   1200
tcttcctgcc gggcgtgccg caggtctact acgtgggcgc gctcgccggc cgcaacgaca   1260
tggaactgct cgcgccgcacc aacaacggcc gcgacatcaa ccgccactac tactccaccg   1320
ccgaaatcga tgaaaacctc gaacgcccgg tggtcaaggc cctgaacgcc ctggccaagt   1380
tccgcaacga actgcctgca ttcgatggcg agttcagcta cgaggtcgat ggcgacacgt   1440
ccatcacctt ccgctggacc gccgccgacg gcacgtccac ggccgccctc accttcgagc   1500
ccggacgcgg cctcggcaca gacaacgcca ccccggttgc cagccttgcc tggagcgatg   1560
ccgccggcga ccacgaaacc cgcgatctgc tcgccaaccc gccgattgcc gatatcgact   1620
aaccgttggc cctaaaacgc cactccgctg tgcgcgctcc aagtagtgcg cccggcgtaa   1680
gctgggttca tggagagcaa accgcccgca gtgcactgaa gccagtgcgc ccgggcggtt   1740
ttgcgtatgc ggggttgaag gtcatgctcc tgcgggcgcg gcccaagcat cccgccggaa   1800
tgcgacgaga cgagcagcag                                               1820
```

<210> SEQ ID NO 2
<211> LENGTH: 1238
<212> TYPE: DNA
<213> ORGANISM: Bifidobacterium longum

<400> SEQUENCE: 2

```
ggcaacacgg ccgtcttcaa gcagaaagcc accacgcaaa cattcctcga aagccttggt     60
tttgccgcta ggtgaaacag gtcaagtgaa aagtaagctc aatactgaag gaaaaaccga    120
aggcaagtcc ttccaaagga gggaatatga ctactgttct ggttacgggc ggtgctggat    180
tcatcgccac tcacaccgac atcgaactgc tcaacaaggg ctacgacgtt atttccgtag    240
ataactacgg caactcgtcg cccgtggcgc ttgagcgcgt cgagcaaatc accggcaagc    300
```

```
cggtcaagcg ttatgacggc gacgtgcgcg atgaggcgct catggaacgc gtcttcgctg      360
aaaacaacat cgactgggtc atccactttg ccggtctcaa ggccgtgggc gagtccgtgg      420
ccaagccgat cgaatactac gacaacaacc tgtactccac gcttgtgctg ctcaaggtga      480
tgaagaagca caacgtcaag aagatcatct tctcatcctc cgccaccgtg tacggcacgc      540
cgaaggaact gccgatcacc gaggagacgc cgaccggcgg caccaccaac ccgtacggca      600
cctccaagct gttccaggag cagattctgc gcgacgtgca tgtggccgat ccgtcctgga      660
ccatcgtgct gctgcgctac ttcaacccgg tcggcgcgca cgagtccggc ctgctgggcg      720
aagacccgaa gggtattccg gcgaacctca ccccgtacgt ggccaaggtc gcggtcggcg      780
agctcaagga agtccaggtc tacgcgacg actacgacac gcccgacggc actggtgtgc      840
gtgactacat ccacgtggtc gacctggcca agggccacgt ggccgtcatt gaccacatcg      900
acaaggaagg cgtgttcgtc tacaacctgg gtactggcca cggctactcc gtgcttgagg      960
ttatcaaggc ttacgagaag gccgccggtc atccgattcc gtacgcgatc aagccgcgtc     1020
gccccggtga catcgccgcc tgctacgccg acgcttccaa ggcggagaag gagcttggct     1080
ggaaggccga gctgaccatc gacgacatgg ccgcctcctc cctcaactgg cagaccaaga     1140
accccaacgg tttccgcgac gcggagtgat atgagcagat gagctccctc tgatgaggga     1200
gctcatctgt cgtttatcac acaatgcgcc tatcggcg                             1238

<210> SEQ ID NO 3
<211> LENGTH: 1346
<212> TYPE: DNA
<213> ORGANISM: Bifidobacterium longum

<400> SEQUENCE: 3
caccagagcg agaccattga ggaaagtgag caaacccatg gctgatttcg ccaactacac       60
ccccggggag tatgcgaagg agcacatccg catcacgccg acgacgcttg ccgacggccg      120
tgacttcttc tacctggacg acgaccccga gttcgtctcc ggtgccaaga cccgcgagct      180
caaggacccg cgcccgctgg actaccgttt cgccccgcac ctggacgccg acggcaacga      240
agtgccgtac gccgccccgc agatgcgccg cgaccgctg accggcgact ggatcccgat      300
ggccaccgcc cgtatgaacc gcccgatcac cgccggcccc ggcgccaccg ccaagggcaa      360
cccgctggcc gcccgcaagc ccggtgaccc gtaccaggac ggcgaagtgc cggacaccga      420
ctacaacgtc gtcgtgttcg agaaccgctt ccctccatg gtgcgcgtgc ccggcgtctc      480
cgaggacgtg acctacgttg acggcaaccc gctgtgggag aagaagctcg ccgccggccg      540
ctgcgaggtc atctgcttcg acccgaacga ggacggcctg ccggccgatc tgccggtctc      600
ccgcctgcgc accgtggttg aggcttgggc cttccgtacc gccgaaatct ccaagatgga      660
aggcatcgag cagatcttcc cgttcgagaa ccacggccag gaaatcggcg tctccctcgc      720
tcacccgcac ggccaggtct actgctaccc gttcatcgcc ccgaagatgg agaaggaact      780
ccagcacacc gaggcctacc acgagaagac cggcggcaac ctgcttaagg acatcatgaa      840
cgccgagctc gaagccggcg aacgcatcgt gatgcgcaac cacagctggg tcgcctacgt      900
gccggccgcc gcccgttggc ccctcgaggt ccacgtggct ccggtgcgcg acgtgctcac      960
cctcgaccag ctcaacgacg aagaacgctg ggacctcgcc tccatgtact cgcacctcct     1020
gaagcgcggc aacgccttct tcgacaaggg cgacggcaag ggcatggacc tgccatacat     1080
cgccgcctgg caccaggccc cgatccacga cgcccgccgc gagaactacc gcctgaacct     1140
gcagttcttc tccttccgcc gcgccgccaa caagatcaag tacctcgccg ctccgaatc     1200
```

| | | |
|---|---|---|
| cggcatggcc gcctggatct ccgacaccac gccggaactc atcgccaagc gcttccacga | 1260 |
| gctcggctcc atcgacatcg ccgactgata gaaagaaaac atcaatgact gctgttgaat | 1320 |
| tcattgagcc gctgacccat gaggaa | 1346 |

<210> SEQ ID NO 4
<211> LENGTH: 2053
<212> TYPE: DNA
<213> ORGANISM: Bifidobacterium longum

<400> SEQUENCE: 4

| | | |
|---|---|---|
| aacatccgcg agaagaagaa gcggaagtga cacgcgcgta atttgccaga tttcaaatat | 60 |
| ctggtaaatt atctactcgg tgcttttgca ccatcgggcc gtagcgcagt ttggtagcgc | 120 |
| acttgactgg gggtcaaggg gtcgcgggtt caaatcccgc cggcccgacc gattagcccc | 180 |
| ggaattctgc cacttttgag tggttgtctt ccggggtttt tccgttttca gacaatatga | 240 |
| gacaacatga cgacggactt acctttgtaa gccattcgta atgaattatc accgacaatt | 300 |
| caccgcctcc gcaccccgt cgtatgcgtt tgccccaaac aggggctaga ctggttccta | 360 |
| ttgatttgac gaaagggacc cgaattgacc gaaataaacg acaaggccca actggatatc | 420 |
| gccgccgctg acgacaccga cgccgtcacc tcggacaccc ccgaagaaac cgtaaacacc | 480 |
| cccgaagtgg atgagacttt cgagctttcg gccgccaaga tgcgcgagca cggcatgagc | 540 |
| gaaaccgcca tcaaccagtt ccaccatttg tatgacgtat ggcgccatga agaagcctcc | 600 |
| agctggattc gtgaggacga catcgagccg cttggccacg tgcccagctt ccacgacgtc | 660 |
| tatgagacca tcaaccacga caaggccgtg gacgccttcg ccaagaccgc attcctcaag | 720 |
| ctcaatggcg gtctgggcac ctccatggga ttagacaagg ccagtcgct gttgccggtg | 780 |
| cgtaggcaca aggccaagca gatgcgcttc atcgacatca tcatcggtca ggtgcttacc | 840 |
| gctcgcaccc gcctgaacgt cgaactgccg ctgacgttca tgaactcctt ccacacttcg | 900 |
| gcggacacga tgaaggcgct caagcatcat cgcaagttca gccagcatga cgtgccgatg | 960 |
| gaaatcatcc agcatcagga acccaaactc gtggccgcca ccggcgaacc ggtgagctac | 1020 |
| cccatgaacc cggagctgga atggtgcccg cccggccacg gcgacctgtt ctccaccatc | 1080 |
| tgggagtccg gcctgcttga cgtattggag gagcgcggct tcaagtacct gttcatctcc | 1140 |
| aattccgaca atctcggtgc acgcccctcg cgtacgttgg cccagcactt cgaaaacaca | 1200 |
| ggtgccccgt ttatggctga agtggccatc cgcaccaagg ccgatcgcaa gggaggccat | 1260 |
| atcgtgcgag acaaggccac tggtcgcctg atcctgcgtg aaatgagcca ggtccatccg | 1320 |
| gatgataagg aagcggccca agacatcgcc aagcatcctt acttcaacac caactcgatc | 1380 |
| tggattcgca tcgacgcttt gaaagacaag ctcgccgaat gcgatggtgt gttgccgttg | 1440 |
| ccggtgattc gtaacaaaaa gaccgtgaat cccacggacc cgaactccga acaggtgatt | 1500 |
| cagctggaaa ccgccatggg tgccgcaatc ggtctgttca acgttccat ctgcgtccaa | 1560 |
| gtggatcgta tgcgcttcct tccggtgaaa accaccaatg atttgttcat tatgcgttcc | 1620 |
| gatcgcttcc acctgacgga cacgtatgag atggaagacg gcaattacat cttcccgaac | 1680 |
| gtcgaacttg atccgcgata ctacaagaac atccgcgatt tcgacgaacg gttccctac | 1740 |
| gccgtgccat ctttggccgc agccaactcg gtttccattc agggcgactg gacattcgga | 1800 |
| cgtgacgtca tgatgttcgc cgacgccaaa cttgaagata aggcgagcc aagctatgtg | 1860 |
| ccgaacggca aatacgttgg tccgcaaggc atcgaaccgg acgattgggt gtgatttaca | 1920 |
| acacggtcga acgataaaaa agatattatt tttgtgaaat ggcgctcaag tgcggaaaaa | 1980 | gcctctaaga tagagtgagt gtgaggaaac tcatacgcac ttataacgaa acagtaacta    2040 tacgtgagga cta    2053

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtccctttcg aggtaatatc gaac    24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgggcgcacg tacggttcca acat    24

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggcaacacgg ccgtcttcaa gcagaaagc    29

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ttcgaatcgc accgagctca cccgctgggc    30

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gatttagtaa aggagctcgt gctggcc    27

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

-continued

```
gaacagcttg gtagcttgcg aaacgcc                                          27

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gaggaattcg gcttcgaagg cacgc                                            25

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
acgtccgctt gtgccctctg ccat                                             24

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tatacatatg aaaaacaaag tgcaactcat c                                     31

<210> SEQ ID NO 14
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggccaactcg aggtcgatat cggcaatcgg cgggttggc                             39

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tatacatatg actactgttc tggttacggg c                                     31

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ctgctcctcg agctccgcgt cgcggaaacc gttggggttc                            40
```

```
<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
caaacatatg gctgatttcg ccaactac                                      28

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ttctgcggcc gcgtcggcga tgtcgatgga                                    30

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
accccatatg accgaaataa acgacaaggc                                    30

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gttgtctcga gcacccaatc gtccggttc                                     29
```

METHOD FOR PRODUCING LACTO-N-BIOSE I AND GALACTO-N-BIOSE

CROSS-REFERENCE TO RELATED APPLICATIONS

The present application is a 35 U.S.C. §371 National Stage patent application of International patent application PCT/JP2007/074362, filed on Dec. 12, 2007, which claims priority to Japanese patent application JP 2006-346470, filed on Dec. 22, 2006.

TECHNICAL FIELD

The present invention relates to a method for producing lacto-N-biose I and galacto-N-biose using an enzyme method.

BACKGROUND ART

Lacto-N-biose I (Galβ1-3GlcNAc) and galacto-N-biose (Galβ1-3GalNAc), which are β1,3-galactosides, have structures often seen in physiologically active sugar chains. They can be applied as functional sugar and the like in food industries and can also be used as pharmaceutical preparations or reagents, such as substrates or inhibitors of enzymes or lectins, and constituent sugars of living bodies.

Examples of a conventionally known method for producing these compounds include a method for producing lacto-N-biose I (JP Patent Publication (Kokai) No. H06-253878 A (1994)), which is characterized by sequentially reacting a substrate containing lactose and N-acetylglucosamine as a starting material with β-galactosidase derived from porcine testis and β-galactosidase produced by *Bacillus circulans*, and a method for producing complex carbohydrates (JP Patent Publication (Kokai) No. 2003-189891 A) using microorganisms, animal cells, or insect cells capable of producing complex carbohydrates from sugar nucleotides and complex carbohydrate precursors. However, the former method exerts low reaction efficiency and the latter method is a method for producing such sugar using a fermentation method. Hence, both methods lack practicality in that production of the compounds always creates rising costs.

JP Patent Publication (Kokai) No. 2005-341883 A suggests that a lacto-N-biose derivative can be synthesized using the reverse reaction catalytic activity of lacto-N-biose phosphorylase, and galactose-1-phosphate as a raw material. However, galactose-1-phosphate is expensive, and thus the method lacks practical value.

DISCLOSURE OF THE INVENTION

Thus, there is a need for methods for inexpensively and easily producing lacto-N-biose I and galacto-N-biose.

As a result of intensive studies, the present inventors have completed a method for producing lacto-N-biose I and galacto-N-biose using an enzyme method.

Specifically, the present invention encompasses the following (1) to (8).

(1) A method for producing lacto-N-biose I, characterized in that the method comprises causing:

(i) a combination of a carbohydrate raw material with an enzyme (G1P synthase) that catalyzes phosphorolysis of the carbohydrate raw material to give α-glucose-1-phosphate; and (ii) a combination of an enzyme that converts α-glucose-1-phosphate to UDP-glucose and an enzyme that converts UDP-galactose to α-galactose-1-phosphate with their cofactors, and/or a combination of an enzyme (UDP-Gly synthase) that converts α-glucose-1-phosphate and UDP-galactose to UDP-glucose and α-galactose-1-phosphate, respectively, with its cofactor(s)

to act in the presence of N-acetylglucosamine, phosphoric acid, lacto-N-biose phosphorylase (EC 2.4.1.211; 1,3β-galactosyl-N-acetylhexosamine phosphlorylase), and UDP-glucose-4-epimerase (EC 5.1.3.2).

(2) The method according to (1) above, wherein the combination of (i) is one or more combinations selected from the group consisting of a combination of sucrose with sucrose phosphorylase (EC 2.4.1.7), a combination of starch or dextrin with phosphorylase (EC 2.4.1.1), a combination of cellobiose with cellobiose phosphorylase (EC 2.4.1.20), a combination of cellodextrin(s) with cellodextrin phosphorylase (EC 2.4.1.49) and cellobiose phosphorylase (EC 2.4.1.20), a combination of laminarioligosaccharide(s) with laminaribiose phosphorylase (EC 2.4.1.31) and/or β-1,3 oligoglucan phosphorylase (EC 2.4.1.30), and a combination of trehalose with trehalose phosphorylase (EC 2.4.1.231).

(3) The method according to (1) above, wherein the combination(s) of (ii) is/are one or more combinations selected from the group consisting of: a combination of UDP-glucose-hexose-1-phosphate uridylyltransferase (EC 2.7.7.12) with UDP-glucose, UDP-galactose, or a mixture thereof; a combination of glucose-1-phosphate uridylyltransferase (EC 2.7.7.9) and galactose-1-phosphate uridylyltransferase (EC 2.7.7.10) with UTP; a combination of glucose-1-phosphate uridylyltransferase (EC 2.7.7.9) and galactose-1-phosphate uridylyltransferase (EC 2.7.7.10) with UDP-glucose and/or UDP-galactose and pyrophosphate; a combination of glucose-1-phosphate uridylyltransferase (EC 2.7.7.9) and galactose-1-phosphate uridylyltransferase (EC 2.7.7.10) with UTP and UDP-glucose and/or UDP-galactose and pyrophosphate; a combination of an enzyme having both activity of glucose-1-phosphate uridylyltransferase and activity of galactose-1-phosphate uridylyltransferase with UTP; a combination of an enzyme having both activity of glucose-1-phosphate uridylyltransferase and activity of galactose-1-phosphate uridylyltransferase with UDP-glucose and/or UDP-galactose and pyrophosphate; and a combination of an enzyme having both activity of glucose-1-phosphate uridylyltransferase and activity of galactose-1-phosphate uridylyltransferase with UTP and UDP-glucose and/or UDP-galactose and pyrophosphate.

(4) The method according to any one of (1) to (3) above, wherein the enzyme is immobilized on a carrier.

(5) A method for producing galacto-N-biose, characterized in that the method comprises causing:

(i) a combination of a carbohydrate raw material with an enzyme (G1P synthase) that catalyzes phosphorolysis of the carbohydrate raw material to give α-glucose-1-phosphate; and (ii) a combination of an enzyme that converts α-glucose-1-phosphate to UDP-glucose and an enzyme that converts UDP-galactose to α-galactose-1-phosphate with their cofactors, and/or a combination of an enzyme (UDP-Gly synthase) that converts α-glucose-1-phosphate and UDP-galactose to UDP-glucose and α-galactose-1-phosphate, respectively, with its cofactor(s)

to act in the presence of N-acetylgalactosamine, phosphoric acid, lacto-N-biose phosphorylase (EC 2.4.1.211), and UDP-glucose-4-epimerase (EC 5.1.3.2).

(6) The method according to (5) above, wherein the combination of (i) is one or more combinations selected from the group consisting of a combination of sucrose with sucrose phosphorylase (EC 2.4.1.7), a combination of starch or dextrin with phosphorylase (EC 2.4.1.1), a combination of cellobiose with cellobiose phosphorylase (EC 2.4.1.20), a combination of cellodextrin(s) with cellodextrin phosphorylase (EC 2.4.1.49) and cellobiose phosphorylase (EC 2.4.1.20), a combination of laminarioligosaccharide(s) with laminaribiose phosphorylase (EC 2.4.1.31) and/or β-1,3 oligoglucan phosphorylase (EC 2.4.1.30), and a combination of trehalose with trehalose phosphorylase (EC 2.4.1.231).

(7) The method according to (5) above, wherein the combination(s) of (ii) is/are one or more combinations selected from the group consisting of: a combination of UDP-glucose-hexose-1-phosphate uridylyltransferase (EC 2.7.7.12) with UDP-glucose, UDP-galactose, or a mixture thereof; a combination of glucose-1-phosphate uridylyltransferase (EC 2.7.7.9) and galactose-1-phosphate uridylyltransferase (EC 2.7.7.10) with UTP; a combination of glucose-1-phosphate uridylyltransferase (EC 2.7.7.9) and galactose-1-phosphate uridylyltransferase (EC 2.7.7.10) with UDP-glucose and/or UDP-galactose and pyrophosphate; a combination of glucose-1-phosphate uridylyltransferase (EC 2.7.7.9) and galactose-1-phosphate uridylyltransferase (EC 2.7.7.10) with UTP and UDP-glucose and/or UDP-galactose and pyrophosphate; a combination of an enzyme having both activity of glucose-1-phosphate uridylyltransferase and activity of galactose-1-phosphate uridylyltransferase with UTP; a combination of an enzyme having both activity of glucose-1-phosphate uridylyltransferase and activity of galactose-1-phosphate uridylyltransferase with UDP-glucose and/or UDP-galactose and pyrophosphate; and a combination of an enzyme having both activity of glucose-1-phosphate uridylyltransferase and activity of galactose-1-phosphate uridylyltransferase with UTP and UDP-glucose and/or UDP-galactose and pyrophosphate.

(8) The method according to any one of (5) to (7) above, wherein the enzyme is immobilized on a carrier.

This description includes part or all of the contents as disclosed in the description and/or drawings of Japanese Patent Application No. 2006-346470, which is a priority document of the present application.

BRIEF DESCRIPTION OF THE DRAWINGS

FIG. 1 shows the results of thin-layer chromatography, demonstrating that lacto-N-biose I can be produced by the method of the present invention from the indicated carbohydrate raw material and enzyme catalyzing phosphorolysis of the carbohydrate raw material.

BEST MODES FOR CARRYING OUT THE INVENTION

The present invention relates to a method for producing lacto-N-biose I or galacto-N-biose using an enzyme method.

Figure 3:
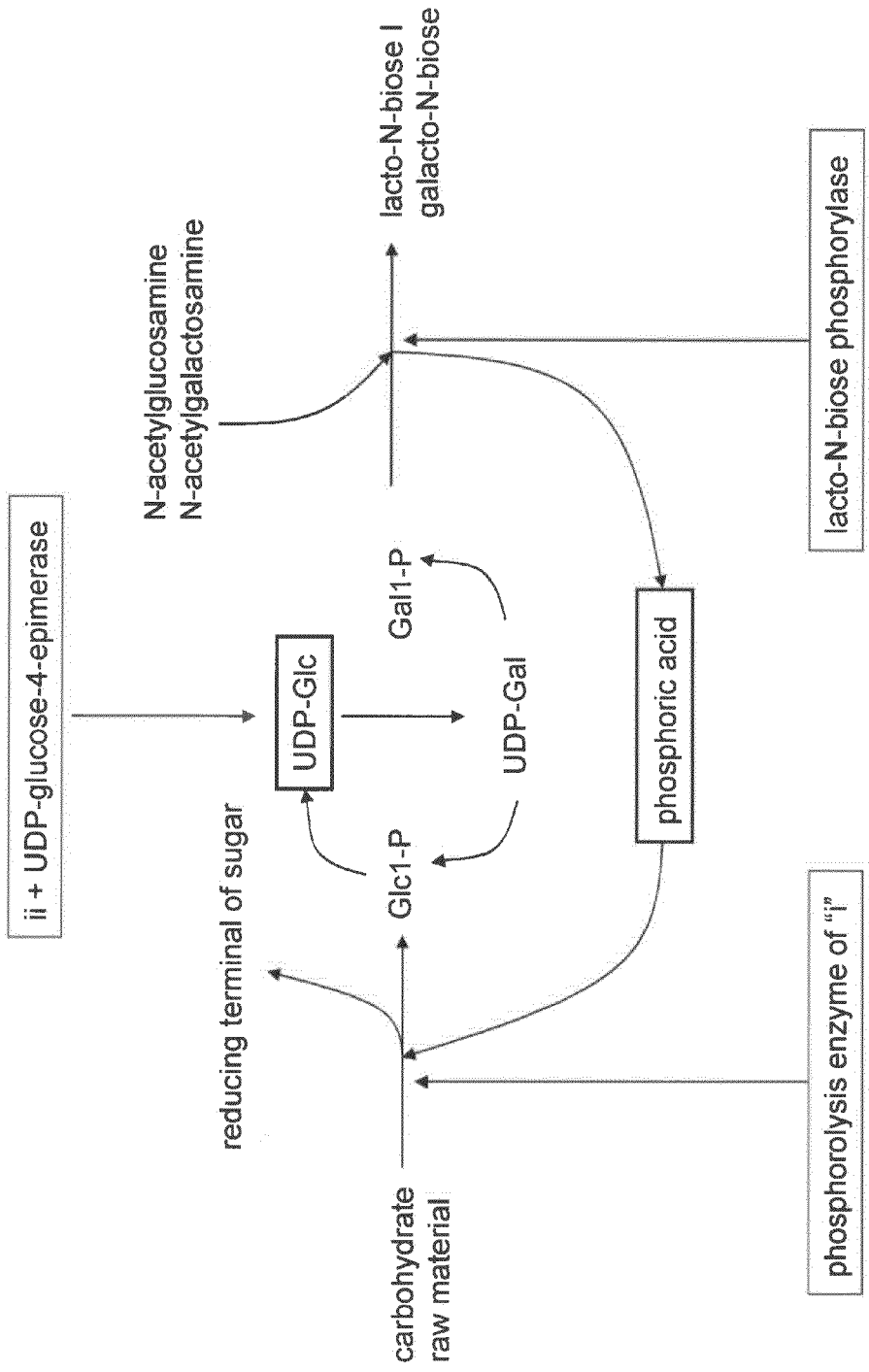
FIG. 3 schematically shows the reaction pathway of the enzyme method of the present invention.

FIG. 3 schematically shows the reaction pathway of the enzyme method of the present invention. As shown in FIG. 3, the enzyme method of the present invention mainly comprises the following three enzyme reactions: (1) a phosphorolytic reaction of a carbohydrate raw material; (2) a reaction for conversion of glucose-1-phosphate to galactose-1-phosphate; and (3) a reaction for synthesis of lacto-N-biose I or galacto-N-biose from N-acetylglucosamine or N-acetylgalactosamine.

The reaction of (1) produces a glucose-1-phosphate and a reducing terminal of sugar via the reaction of a combination of a carbohydrate raw material and an enzyme (G1P synthase) that catalyzes phosphorolysis of the carbohydrate raw material to give α-glucose-1-phosphate contained as the above factor (i), in the presence of phosphoric acid. Examples of the combination of the carbohydrate raw material and the enzyme used as the above factor (i) include, but are not limited to, any one of: a combination of sucrose with sucrose phosphorylase; a combination of starch or dextrin with phosphorylase; a combination of cellobiose with cellobiose phosphorylase; a combination of cellodextrin(s) with cellodextrin phosphorylase and cellobiose phosphorylase; a combination of laminarioligosaccharide(s) with laminaribiose phosphorylase; and a combination of trehalose with trehalose phosphorylase; or a combination thereof. Examples of a more preferable combination include any one of: a combination of sucrose with sucrose phosphorylase; a combination of cellobiose with cellobiose phosphorylase; a combination of cellodextrin(s) with cellodextrin phosphorylase and cellobiose phosphorylase; and a combination of starch or dextrin with phosphorylase; or a combination thereof. The most preferable combination is a combination of sucrose with sucrose phosphorylase. The concentration of a carbohydrate raw material to be used herein is not limited, but preferably ranges from approximately 1 to approximately 1000 g/L, and more preferably ranges from approximately 10 to approximately 1000 g/L. The form of G1P synthase to be used herein is not particularly limited. Various forms of the G1P synthase can be used, such as cell extracts, purified enzymes, and immobilized enzymes. The amount of the G1P synthase to be used herein is also not particularly limited. For example, approximately 0.1 units to approximately 100 units of the G1P synthase can be used per gram of a carbohydrate raw material.

Moreover, phosphoric acid involved in the above reaction may be of any origin. The concentration of phosphoric acid to be added to the reaction system is not particularly limited, but preferably ranges from approximately 0.1 mM to approximately 1000 mM, and more preferably ranges from approximately 1 mM to approximately 100 mM.

The reaction of the above (2) coverts, in the presence of UDP-glucose-4-epimerase and with the use of a combination(s) of an enzyme(s) and cofactor(s) contained as the above factor (ii), glucose-1-phosphate produced by the reaction of the above (1) to UDP-Glc and converts UDP-Gal to galactose-1-phosphate.

Examples of an enzyme(s) to be used as the factor (ii) include any one of: a combination of an enzyme that converts α-glucose-1-phosphate to UDP-glucose and an enzyme that converts UDP galactose to galactose-1-phosphate; and an enzyme (UDP-Gly synthase) that converts α-glucose-1-phosphate and UDP-galactose to UDP-glucose and α-galactose-1-phosphate, respectively; or a combination thereof. Specifically, the enzyme(s) or enzyme combination contained as the factor (ii), proceeds the conversion reaction of the above (2) that converts α-glucose-1-phosphate to α-galactose-1-phosphate in the presence of a cofactor(s) for proceeding the reaction by the enzyme(s) or enzyme combination, and UDP-glucose-4-epimerase.

Therefore, examples of the combination of the above factor (ii) intended in the present invention include the following combinations: a combination of UDP-glucose-hexose-1-phosphate uridylyltransferase (EC 2.7.7.12) with UDP-glucose, UDP-galactose, or a mixture thereof; a combination of glucose-1-phosphate uridylyltransferase (EC 2.7.7.9) and galactose-1-phosphate uridylyltransferase (EC 2.7.7.10) with UTP; a combination of glucose-1-phosphate uridylyltransferase (EC 2.7.7.9) and galactose-1-phosphate uridylyltransferase (EC 2.7.7.10) with UDP-glucose and/or UDP-galactose and pyrophosphate; a combination of glucose-1-phosphate uridylyltransferase (EC 2.7.7.9) and galactose-1-phosphate uridylyltransferase (EC 2.7.7.10) with UTP and UDP-glucose and/or UDP-galactose and pyrophosphate; a combination of an enzyme (among EC 2.7.7.9 and EC 2.7.7.10 enzymes, enzymes having both activity of glucose-1-phosphate uridylyltransferase and activity of galactose-1-phosphate uridylyltransferase may exist) having both activity of glucose-1-phosphate uridylyltransferase and activity of galactose-1-phosphate uridylyltransferase with UTP; a combination of an enzyme having both activity of glucose-1-phosphate uridylyltransferase and activity of galactose-1-phosphate uridylyltransferase with UDP-glucose and/or UDP-galactose and pyrophosphate; and a combination of an enzyme having both activity of glucose-1-phosphate uridylyltransferase and activity of galactose-1-phosphate uridylyltransferase with UTP and UDP-glucose and/or UDP-galactose and pyrophosphate. Preferably, the combination of the above factor (ii) is: a combination of UDP-glucose-hexose-1-phosphate uridylyltransferase (EC 2.7.7.12) with UDP-glucose or UDP-galactose or both of them; a combination of an enzyme having both activity of glucose-1-phosphate uridylyltransferase and activity of galactose-1-phosphate uridylyltransferase with UTP; a combination of an enzyme having both activity of glucose-1-phosphate uridylyltransferase and activity of galactose-1-phosphate uridylyltransferase with UDP-glucose and/or UDP-galactose and pyrophosphate; or a combination of an enzyme having both activity of glucose-1-phosphate uridylyltransferase and activity of galactose-1-phosphate uridylyltransferase with UTP and UDP-glucose and/or UDP-galactose and pyrophosphate. The combinations in (ii) may be used alone or in combination.

These enzymes are not particularly limited and enzymes of any origin can be used herein. The forms of such enzymes to be used herein are not particularly limited and various forms thereof can be used, such as cell extracts, purified enzymes, and immobilized enzymes. The amounts of such enzymes to be used herein are also not particularly limited. For example, approximately 1 unit to approximately 1000 units of such enzymes can be used per gram of a carbohydrate raw material. The concentration of a cofactor to be used herein is not particularly limited, but preferably ranges from approximately 0.01 mM to approximately 100 mM and more preferably ranges from approximately 0.02 mM to approximately 10 mM.

UDP-glucose-4-epimerase is not particularly limited and the enzyme of any origin can be used herein. The form of UDP-glucose-4-epimerase to be used herein is not particularly limited. Various forms of the enzyme can be used herein, such as cell extracts, purified enzymes, and immobilized enzymes. The amount of the enzyme to be used herein is also not particularly limited. For example, approximately 0.1 units to approximately 100 units of the enzyme can be used per gram of a carbohydrate raw material.

The reaction of the above (3) synthesizes, in the presence of lacto-N-biose phosphorylase and with the use of N-acetylglucosamine or N-acetylgalactosamine as a starting material, lacto-N-biose I or galacto-N-biose from galactose-1-phosphate produced by the above reaction (2). The concentration of N-acetylglucosamine or N-acetylgalactosamine used as a starting material is not particularly limited, but preferably ranges from approximately 10 mM to approximately 2 M and more preferably ranges from approximately 100 mM to approximately 1 M. Lacto-N-biose phosphorylase of any origin can be used herein. Preferably, the enzyme from the bacteria of the genus *Bifidobacterium* (e.g., JP Patent Publication (Kokai) No. 2005-341883 A) is used. The form of lacto-N-biose phosphorylase to be used herein is not particularly limited and various forms thereof can be used, such as cell extracts, purified enzymes, and immobilized enzymes. The amount of lacto-N-biose phosphorylase to be used herein is also not particularly limited. For example, approximately 0.1 units to approximately 100 units of lacto-N-biose phosphorylase can be used per gram of a carbohydrate raw material.

The amounts of the above enzymes used in the present invention are as defined below: 1 unit of lacto-N-biose phosphorylase is the enzyme level at which 1 micromole of phosphoric acid is liberated per minute in a reaction solution comprising 0.1 M MOPS buffer (pH 7.5), 10 mM galactose-1-phosphate, and 1 M N-acetylglucosamine; 1 unit of UDP-glucose-hexose-1-phosphate uridylyltransferase is the enzyme level at which 1 micromole of glucose-1-phosphate is generated per minute in a reaction solution comprising 0.1 M MOPS buffer (pH 7.5), 10 mM galactose-1-phosphate, 10 mM UDP-glucose, and 10 mM magnesium chloride; 1 unit of UDP-glucose-4-epimerase is the enzyme level at which 1 micromole of UDP-glucose is generated per minute in a reaction solution comprising 0.1 M MOPS buffer (pH 7.5) and 5 mM UDP-galactose; 1 unit of a phosphorylase enzyme such as sucrose phosphorylase is the enzyme level at which 1 micromole of glucose-1-phosphate is generated per minute in a reaction solution comprising 0.1 M MOPS buffer (pH 7.5), a substrate (carbohydrate raw material) such as 10 mM sucrose, and 10 mM sodium hydrogenphosphate; and 1 unit of an enzyme having both activity of glucose-1-phosphate uridylyltransferase and activity of galactose-1-phosphate uridylyltransferase is the enzyme level at which 1 micromole of glucose-1-phosphate is generated per minute in a reaction solution comprising 0.1 M MOPS buffer (pH 7.5), 10 mM pyrophosphate, 10 mM UDP-glucose, and 10 mM magnesium chloride.

The above-mentioned enzymes of the present invention may be of any origin. For example, they may be any enzymes from prokaryotes such as bacteria or from eukaryotes such as yeast, fungus, and animal. They may also be recombinant enzymes. Commercially available enzymes can be used as such enzymes. Alternatively, such enzymes may be purified from the nature by methods known to persons skilled in the art or may be obtained by use of gene recombination methods, for example. For example, in a gene recombination method, an enzyme of the present invention is generated by carrying out PCR using primers designed based on the nucleotide sequence of the enzyme gene that is described in a document or registered in a known nucleic acid or protein sequence database, so as to amplify cDNA prepared from mRNA corresponding to the enzyme gene in an appropriate library, incorporating the cDNA into a commercially available gene expression vector, transforming a bacterial cell such as *Escherichia coli* with the expression vector, and allowing the enzyme to be generated within the cell. The generated enzyme can be purified by a protein purification method known to persons skilled in the art, such as crude fractionation (e.g., ammonium sulfate fractionation) or various types of column chromatography, for example. Also, the purification can be facilitated by expressing an enzyme in the form of fusion protein with GST or His-tag.

As a nucleic acid or protein sequence database, sequences included in GenBank, UniGene, EMBL, or the like can be used. Examples of a program that can be used as a sequence search program include BLAST and FASTA.

A primer is generally 17 to 30 bases in length and is preferably 19 to 25 bases in length. PCR reaction can be conducted by use of a target enzyme gene or the corresponding cDNA as a template and a sense primer and antisense primer having the above length (containing the 5' end or the 3' end of said gene or cDNA, respectively) synthesized with an automatic DNA synthesizer. PCR is generally conducted such that in the presence of a target template DNA, primers, 4 types of bases (dNTPs), and heat stable DNA polymerase, 20 to 40 cycles each consisting of denaturation, annealing, and elongation are carried out. Denaturation is a process for dissociating double-stranded DNA into single strands, which is generally carried out at 94° C. for 15 seconds to 5 minutes. Annealing is a process for annealing a single-stranded template DNA and primers complementary thereto, which is generally carried out at 55° C. to 60° C. for 30 seconds to 2 minutes. Elongation is a reaction for elongation of primers along the template DNA, which is generally carried out at 72° C. for 30 seconds to 10 minutes.

Transformation can be carried out using techniques as described in Sambrook et al., Molecular Cloning, A Laboratory Manual (1989). Cold Spring Harbor Laboratory Press, for example.

The enzymes of the present invention can also be directly purified from the above prokaryotic cells or eukaryotic cells. A target enzyme can be purified by preparing a cell disrupted solution and then carrying out an appropriate combination of general techniques for enzyme purification, such as centrifugation, ammonium sulfate fractionation, dialysis, various types of chromatography (e.g., gel filtration chromatography, ion exchange chromatography, hydrophobic interaction chromatography, and affinity chromatography), electrophoresis, ultrafiltration, and crystallization. The forms of enzymes that can be used in the present invention may be purified enzymes, or crude enzymes (e.g., cell extracts and freeze-dried products). When a crude enzyme is used, factors that interfere with the above reactions of the present invention should not be contained.

Furthermore, in the present invention, the above enzymes can be immobilized on carriers and then used. Examples of a method for preparing an immobilized enzyme, which can be used in the present invention, include methods known to persons skilled in the art, such as a carrier binding method (e.g., a physical adsorption method, an ion binding method, a covalent binding method, and a biochemically specific binding method), a crosslinking method, and entrapment. The carrier binding method is a method for binding an enzyme to a water-insoluble carrier. In this method, a derivative of polysaccharide such as cellulose, dextran, and agarose, a synthetic polymer such as polyacrylamide gel, a polystyrene resin, and an ion exchange resin, and an inorganic material such as a porous glass and metal oxide can be used as a carrier, for example. The crosslinking method is a method for immobilizing enzymes, which involves reacting a reagent having 2 or more functional groups with enzymes and then crosslinking between the enzymes. As a crosslinking reagent, glutaraldehyde, an isocyanate derivative, N,N-ethylene-bis-maleimide, bis-diazo-benzidine, N,N-polymethylene-bis-iodoacetamide, or the like can be used. Examples of entrapment include lattice entrapment in which an enzyme is entrapped within gel matrix of natural polymers or synthetic polymers. Examples of a macromolecular compound used in such method include polyacrylamide gel, polyvinyl alcohol, a light curing resin, starch, konjac flour, gelatin, alginic acid, and carrageenan.

According to a preferred embodiment of the present invention, the present method can be carried out using a bioreactor column on which all enzymes involved in the above reactions have been immobilized, as an enzyme-immobilized reactor. In this case, lacto-N-biose I and galacto-N-biose can be produced by continuously running an aqueous solution containing a raw material(s) and a cofactor(s) through the column at a certain flow rate (ex. residence time ranging from 0.01 hours to 300 hours).

The mode of the reactions is not particularly limited, but the reactions are generally carried out in an aqueous solution or a buffer. The pH of a reaction solution preferably ranges from 5 to 9. The reaction temperature is not particularly limited, but preferably ranges from 5° C. to 80° C. and more preferably ranges from 20° C. to 60° C. The time for reaction is not particularly limited, but preferably ranges from 0.1 to 3000 hours.

An advantage of the present invention is that the above all enzyme reactions can be carried out conveniently and easily in one container or with the use of a bioreactor. Moreover, the above reactions (1) to (3) can be reversible based on the properties of enzymes involved in the reactions. Hence, overall reactions can be simple equilibration reactions, so that phosphoric acid resulting from the above reaction (3) and UDP-glucose and/or UDP-galactose resulting from the above reaction (2) can be recycled. Therefore, the presence of only catalytic amounts of these substances is required, leading to high cost effectiveness.

Lacto-N-biose I and galacto-N-biose obtained according to the present invention can be purified by any methods. For example, lacto-N-biose I and galacto-N-biose obtained according to the present invention can be isolated by column chromatography or crystallization. Examples of column chromatography include, but are not limited to, size exclusion chromatography, silica gel column chromatography, ion exchange chromatography, ultrafilter separation, and reverse osmosis membrane separation. Examples of a crystallization method include, but are not limited to, condensation, reduction in temperature, and addition of a solvent (e.g., ethanol, methanol, and acetone).

The present invention will be described in more detail below with reference to examples below. However, the scope of the present invention is not limited to such examples.

Example 1

Preparation of Enzyme

For the synthesis of lacto-N-biose I using sucrose as a carbohydrate raw material, to obtain lacto-N-biose phosphorylase, sucrose phosphorylase, UDP-glucose-4-epimerase, UDP-glucose-hexose-1-phosphate uridylyltransferase, and an enzyme having both activity of glucose-1-phosphate uridylyltransferase and activity of galactose-1-phosphate uridylyltransferase, the enzyme genes were isolated from the genomic DNA of *Bifidobacterium longum* JCM1217 strain. The lacto-N-biose phosphorylase gene was obtained by a method described in JP Patent Publication (Kokai) No. 2005-341883 A. For each gene of sucrose phosphorylase (BL0536; SEQ ID NO: 1), UDP-glucose-4-epimerase (BL1644; SEQ ID NO: 2), UDP-glucose-hexose-1-phosphate uridylyltransferase (BL1211; SEQ ID NO: 3), and the enzyme (BL0739; SEQ ID NO: 4) having both activity of glucose-1-phosphate uridylyltransferase and activity of galactose-1-phosphate uridylyltransferase, primers were designed based on the nucleotide sequence of the enzyme gene registered in the genome database of the *Bifidobacterium longum* NCC2705 strain (SEQ ID NOS: 5 to 20; see Table 1).

mM UDP-glucose, and 10 mM magnesium chloride. One (1) unit of UDP-glucose-4-epimerase was determined to be the enzyme level at which 1 micromole of UDP-glucose was generated per minute in a reaction solution comprising 0.1 M

TABLE 1

|  | Primers for cloning | Primers for construction of expression vectors | Yield per liter of culture solution |
|---|---|---|---|
| BL1641 |  |  | 60 mg |
| BL0536 Forward | GTCCCTTTCGAGGTAATATCGAAC (SEQ ID NO: 5) | TATACATATGAAAAACAAAGTGCAACTCATC (SEQ ID NO: 13) | 80 mg |
| Reverse | CGGGCGCACGTACGGTTCCAACAT (SEQ ID NO: 6) | GGCCAACTCGAGGTCGATATCGGCAATCGGCGGGTTGGC (SEQ ID NO: 14) |  |
| BL1644 Forward | GGCAACACGGCCGTCTTCAAGCAGAAAGC (SEQ ID NO: 7) | TATACATATGACTACTGTTCTGGTTACGGGC (SEQ ID NO: 15) | 120 mg |
| Reverse | TTCGAATCGCACCGAGCTCACCCGCTGGGC (SEQ ID NO: 8) | CTGCTCCTCGAGCTCCGCGTCGCGGAAACCGTTGGGGTTC (SEQ ID NO: 16) |  |
| BL1211 Forward | GATTTAGTAAAGGAGCTCGTGCTGGCC (SEQ ID NO: 9) | CAAACATATGGCTGATTTCGCCAACTAC (SEQ ID NO: 17) | 60 mg |
| Reverse | GAACAGCTTGGTAGCTTGCGAAACGCC (SEQ ID NO: 10) | TTCTGCGGCCGCGTCGGCGATGTCGATGGA (SEQ ID NO: 18) |  |
| BL0739 Forward | GAGGAATTCGGCTTCGAAGGCACGC (SEQ ID NO: 11) | ACCCCATATGACCGAAATAAACGACAAGGC (SEQ ID NO: 19) | 20 mg |
| Reverse | ACGTCCGCTTGTGCCCTCTGCCAT (SEQ ID NO: 12) | GTTGTCTCGAGCACCCAATCGTCCGGTTC (SEQ ID NO: 20) |  |

Polymerase chain reaction (PCR) was carried out using these primers, and genomic DNA extracted from the *Bifidobacterium longum* JCM1217 strain as a template, whereby clear 1346-bp, 1238-bp, 1820-bp, and 2053-bp bands having DNA nucleotide sequences were obtained. The obtained bands (PCR products) were analyzed with a DNA sequencer so as to decode the DNA nucleotide sequences (see SEQ ID NOS: 1 to 4 in the Sequence Listing). The DNA nucleotide sequences were translated into amino acids, so that 1251-bp, 1023-bp, 1627-bp, and 1530-bp open reading frames (ORFs) each having high homology with the *Bifidobacterium longum* NCC2705 strain-derived gene were confirmed. To demonstrate that these ORFs are the enzyme genes of interest, the full-length ORFs were amplified by PCR using primers (see Table 1) corresponding to the 5' and the 3' ends of the ORFs, and then they were ligated to a commercial pET30 plasmid for gene expression using the introduced restriction enzyme sites. *Escherichia coli* was transformed with the plasmid by a conventional method, thereby obtaining a transformant. The obtained transformant was cultured at 30° C. and then recombinant enzymes were purified from the cell after induction of gene expression. Purification was carried out using a histidine tag sequence added to the C terminus of each enzyme and a nickel column. The amounts of enzymes each purified from 1 L of a culture solution are as listed in Table 1. Since each of the produced recombinant enzymes had enzyme activity, it was confirmed that each of the cloned genes was the enzyme gene of interest. The activity of each enzyme was as defined below. Incidentally, the reaction temperature employed herein was 30° C. in all cases. One (1) unit of lacto-N-biose phosphorylase was determined to be the enzyme level at which 1 micromole of phosphoric acid was liberated per minute in a reaction solution comprising 0.1 M MOPS buffer (pH 7.5), 10 mM galactose-1-phosphate, and 1 M N-acetylglucosamine. One (1) unit of UDP-glucose-hexose-1-phosphate uridylyltransferase was determined to be the enzyme level at which 1 micromole of glucose-1-phosphate was generated per minute in a reaction solution comprising 0.1 M MOPS buffer (pH 7.5) and 10 mM galactose-1-phosphate, 10

MOPS buffer (pH 7.5) and 5 mM UDP-galactose. One (1) unit of sucrose phosphorylase was determined to be the enzyme level at which 1 micromole of glucose-1-phosphate was generated per minute in a reaction solution comprising 0.1 M MOPS buffer (pH 7.5), 10 mM sucrose, and 10 mM sodium hydrogenphosphate. One (1) unit of an enzyme having both activity of glucose-1-phosphate uridylyltransferase and activity of galactose-1-phosphate uridylyltransferase was determined to be the enzyme level at which 1 micromole of glucose-1-phosphate was generated per minute in a reaction solution comprising 0.1 M MOPS buffer (pH 7.5), 10 mM pyrophosphate, 10 mM UDP-glucose, and 10 mM magnesium chloride.

Cellobiose phosphorylase (Acta Cryst., D60, 1877-1878 (2004)) and laminaribiose phosphorylase (Arch. Biochem. Biophys., 304 (2), 508-514 (1993)) were each prepared by the methods described in the document in parentheses. As phosphorylase, a rabbit-muscle-derived enzyme was purchased from Sigma-Aldorich.

Example 2

Conversion of Sucrose to Lacto-N-Biose I

Conversion reaction from sucrose as a carbohydrate raw material to lacto-N-biose I was carried out. The amount of the reaction solution was 1 milliliter. A substrate solution comprising 0.24 M sucrose, 0.24 M N-acetylglucosamine, 10 mM magnesium chloride, 30 mM phosphate-sodium buffer (pH 7.0), and 1 mM UDP-glucose at final concentrations was prepared. To the solution, 2 U of lacto-N-biose phosphorylase, 20 U of UDP-glucose-4-epimerase, 2.6 U of UDP-glucose-hexose-1-phosphate uridylyltransferase, and 2 U of sucrose phosphorylase, were added per milliliter of the solution, followed by 90 hours of reaction at 30° C. After the reaction was stopped by 10 minutes of boiling, the pH of the reaction solution was adjusted to 4.5 and invertase treatment was carried out so as to degrade the remaining sucrose. The reaction solution was analyzed with TLC (solvent acetonitrile-water 75:25; carrier silica gel 60). As a result, the concentration of lacto-N-biose I was 200 mM. (FIG. 1, lanes 2 and 3)

Example 3

Conversion of Cellobiose to Lacto-N-Biose I

Conversion reaction from cellobiose as a carbohydrate raw material to lacto-N-biose I was carried out. The amount of the reaction solution was 1 milliliter. A substrate solution comprising 0.24 M cellobiose, 0.24 M N-acetylglucosamine, 10 mM magnesium chloride, 30 mM phosphate-sodium buffer (pH7.0), and 1 mM UDP-glucose at final concentrations was prepared. To the solution, 2 U of lacto-N-biose phosphorylase, 20 U of UDP-glucose-4-epimerase, 2.6 U of UDP-glucose-hexose-1-phosphate uridylyltransferase, and 10 U of cellobiose phosphorylase, were added per milliliter of the solution, followed by 90 hours of reaction at 30° C. After the reaction was stopped by 10 minutes of boiling, the pH of the reaction solution was adjusted to 5 and then β glucosidase treatment was carried out so as to degrade the remaining sucrose. The reaction solution was analyzed with TLC (solvent acetonitrile-water 75:25; carrier silica gel 60). As a result, the concentration of lacto-N-biose I was 80 mM. (FIG. 1, lanes 4 and 5)

Example 4

Conversion of Laminaribiose to Lacto-N-Biose I

Conversion reaction from laminaribiose as a carbohydrate raw material to lacto-N-biose I was carried out. The amount of the reaction solution was 1 milliliter. A substrate solution comprising 0.24 M laminaribiose, 0.24 M N-acetylglucosamine, 10 mM magnesium chloride, 30 mM phosphate-sodium buffer (pH7.0), and 1 mM UDP-glucose at final concentrations was prepared. To the solution, 2 U of lacto-N-biose phosphorylase, 20 U of UDP-glucose-4-epimerase, 2.6 U of UDP-glucose-hexose-1-phosphate uridylyltransferase, and 5 U of laminaribiose phosphorylase, were added per milliliter of the solution, followed by 90 hours of reaction at 30° C. After the reaction was stopped by 10 minutes of boiling, the pH of the reaction solution was adjusted to 5 and then β glucosidase treatment was carried out so as to degrade the remaining sucrose. The reaction solution was analyzed with TLC (solvent acetonitrile-water 75:25; carrier silica gel 60). As a result, the concentration of lacto-N-biose I was 80 mM. (FIG. 1, lanes 6 and 7)

Example 5

Conversion of Maltoheptaose to Lacto-N-Biose I

Conversion reaction from maltoheptaose as a carbohydrate raw material to lacto-N-biose I was carried out. The amount of the reaction solution was 1 milliliter. A substrate solution comprising 0.24 M maltoheptaose, 0.24 M N-acetylglucosamine, 10 mM magnesium chloride, 30 mM phosphate-sodium buffer (pH7.0), and 1 mM UDP-glucose at final concentrations was prepared. To the solution, 2 U of lacto-N-biose phosphorylase, 20 U of UDP-glucose-4-epimerase, 2.6 U of UDP-glucose-hexose-1-phosphate uridylyltransferase, and 7 U of phosphorylase, were added per milliliter of the solution, followed by 90 hours of reaction at 30° C. The reaction solution was analyzed with TLC (solvent acetonitrile-water 75:25; carrier silica gel 60). As a result, the concentration of lacto-N-biose I was 100 mM. (FIG. 1, lanes 8 and 9)

Example 6

Preparation of Lacto-N-Biose I from Sucrose

Lacto-N-biose I was synthesized as follows. The amount of the reaction solution was 10 milliliters. A substrate solution comprising 0.66 M sucrose, 0.60 M N-acetylglucosamine, 10 mM magnesium chloride, 30 mM phosphate-sodium buffer (pH 7.0), and 1 mM UDP-glucose at final concentrations was prepared. To the solution, 0.25 U of lacto-N-biose phosphorylase, 0.08 U of sucrose phosphorylase, 2.50 U of UDP-glucose-4-epimerase, and 0.33 U of UDP-glucose-hexose-1-phosphate uridylyltransferase, were added per milliliter of the solution, followed by 500 hours of reaction at 30° C. The concentration of lacto-N-biose I in the reaction solution was approximately 0.52 M and approximately 80% of the carbohydrate raw material was converted to lacto-N-biose I. To degrade unreacted sucrose in the reaction solution, the pH of the reaction solution was adjusted to 4.5 with hydrochloric acid. Three (3) mg of invertase (purchased from Sigma) was added, followed by 15 hours of treatment at 37° C. After treatment, the reaction solution was subjected to a TOYOPEARL HW40F column, and then a lacto-N-biose I fraction was isolated and recovered by gel filtration. The recovered fraction was concentrated using an evaporator and then subjected to freeze-drying, whereby 0.95 g of a lacto-N-biose I product (isolation yield 41%) was obtained.

Example 7

Preparation of Galacto-N-Biose from Sucrose

Galacto-N-biose was synthesized as follows. The amount of the reaction solution was 10 milliliters. A substrate solution comprising 0.66 M sucrose, 0.60 M N-acetylgalactosamine, 10 mM magnesium chloride, 30 mM phosphate-sodium buffer (pH7.0), and 1 mM UDP-glucose at final concentrations was prepared. To the solution, 0.25 U of lacto-N-biose phosphorylase, 0.08 U of sucrose phosphorylase, 2.50 U of UDP-glucose-4-epimerase, and 0.33 U of UDP-glucose-hexose-1-phosphate uridylyltransferase, were added per milliliter of the solution, followed by 500 hours of reaction at 30° C. The concentration of galacto-N-biose in the reaction solution was approximately 0.40 M. Approximately 60% of the carbohydrate raw material was converted to galacto-N-biose. To degrade unreacted sucrose in the reaction solution, the pH of the reaction solution was adjusted to 4.5 with hydrochloric acid. Three (3) mg of invertase (purchased from Sigma) was added, followed by 15 hours of treatment at 37° C. After treatment, the reaction solution was subjected to a TOYOPEARL HW40F column, and then a galacto-N-biose fraction was isolated and recovered by gel filtration. The recovered fraction was concentrated using an evaporator and then subjected to freeze-drying, whereby 0.78 g of a galacto-N-biose product (isolation yield 34%) was obtained.

Example 8

Bulk Preparation of Lacto-N-Biose I

Figure 2:
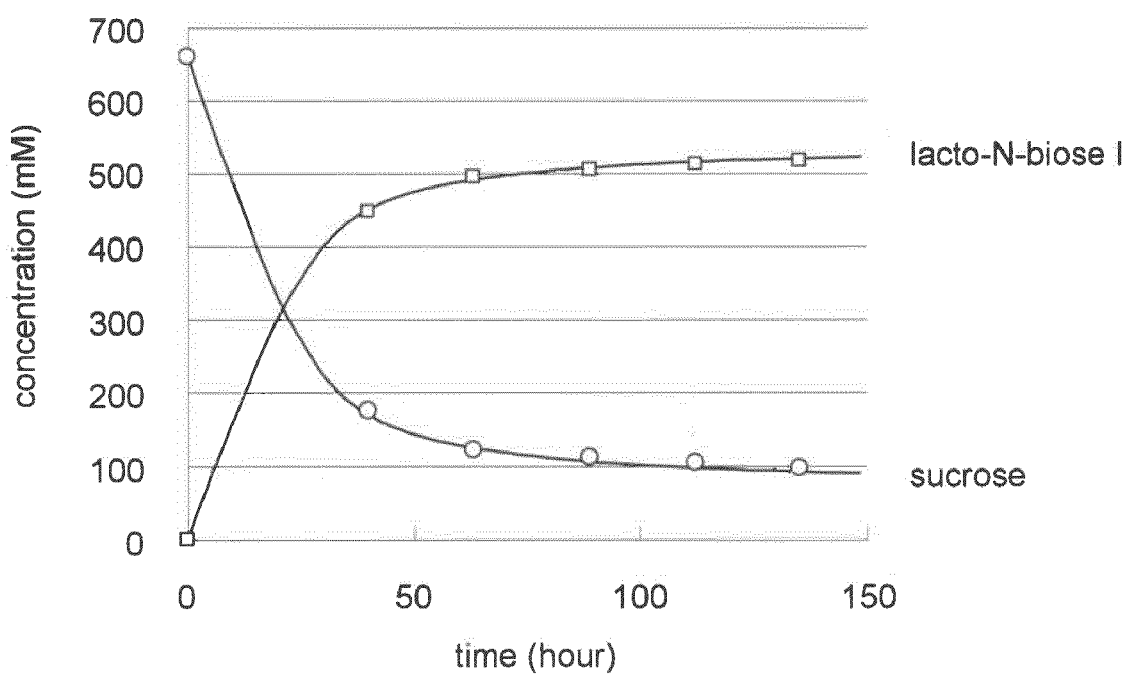
FIG. 2 shows changes in the concentrations of sucrose and lacto-N-biose I over time during implementation of the method for producing lacto-N-biose I of the present invention using sucrose as a carbohydrate raw material.

Bulk preparation of lacto-N-biose I was carried out as follows. The amount of the reaction solution was 1 liter. A substrate solution comprising 0.66 M sucrose, 0.60 M N-acetylglucosamine, 10 mM magnesium chloride, 30 mM phosphate-sodium buffer (pH 7.0), and 1 mM UDP-glucose at final concentrations was prepared. To the solution, 2 U of lacto-N-biose phosphorylase, 0.3 U of sucrose phosphorylase, 20 U of UDP-glucose-4-epimerase, and 2.6 U of UDP-glucose-hexose-1-phosphate uridylyltransferase, were added per milliliter of the solution, followed by 135 hours of reaction at 30° C. Changes over time in the concentration of sucrose and the concentration of lacto-N-biose I are shown in FIG. 2. The reaction yield was 87%. After completion of the reaction, 160 mL of DEAE-TOYOPEARL 650 M equilibrated with 25 mM phosphate buffer (pH 7.0) was added to the reaction solution. The solution was stirred for 1 hour, so that enzymes were adsorbed. A supernatant was then separated by filtration. Twenty (20) grams of dry yeast (Nisshin Camellia) was added to the supernatant and then the mixture was stirred at 30° C. for 18 hours, so that yeast treatment was carried out. After treatment, a supernatant from which yeast had been removed was obtained by centrifugation and filtration using sellite. The obtained supernatant was concentrated using an evaporator and then left to stand at room temperature, so that crystals were obtained. The crystals were separated by filtration and then a product was obtained by vacuum drying. Also, crystallization was carried out again for the mother liquor from which crystals had been separated, so as to improve the recovery rate. As a result, 130 grams of lacto-N-biose I with purity of 97% (yield 55%) and 65 grams of lacto-N-biose I with purity of 85% (yield 24%, total yield 79%) were obtained.

Example 9

Preparation of Lacto-N-Biose I Using Bioreactor

A bioreactor column (φ2.6 cm×30 cm) was prepared by filling a glass column (with a diameter of 2.6 cm) with DEAE-TOYOPEARL 650 M (160 mL) prepared in Example 8, to which the enzymes had been adsorbed. Approximately 2000 U of lacto-N-biose phosphorylase, 300 U of sucrose phosphorylase, 200000 U of UDP-glucose-4-epimerase, and 2600 U of UDP-glucose-hexose-1-phosphate uridylyltransferase, had been adsorbed to the column. A substrate solution (500 ml, containing 0.66 M sucrose, 0.60 M N-acetylglucosamine, 10 mM magnesium chloride, 30 mM phosphate-sodium buffer (pH 7.0), and 1 mM UDP-glucose at final concentrations) was subjected to the column under conditions of 30° C. and a flow rate of 0.1 ml per minute (residence time: 27 hours) for circulation. After the $1^{st}$ column circulation, the concentration of lacto-N-biose I in the substrate solution was approximately 0.3 M, after the $2^{nd}$ column circulation, the same was 0.4 M, and after the $3^{rd}$ column circulation, the same was 0.5 M.

Example 10

Preparation of Lacto-N-Biose I Using Enzyme Having Both Activity of Glucose-1-Phosphate Uridylyltransferase (EC 2.7.7.9) and Activity of Galactose-1-Phosphate Uridylyltransferase (EC 2.7.7.10)

Lacto-N-biose I was synthesized as follows. The amount of the reaction solution was 1 milliliter. A substrate solution comprising 0.66 M sucrose, 0.60 M N-acetylglucosamine, 10 mM magnesium chloride, 30 mM phosphoric acid buffer (pH 7.0), and 1 mM UTP at final concentrations was prepared. To the solution, 0.25 U of lacto-N-biose phosphorylase, 0.08 U of sucrose phosphorylase, 2.5 U of UDP-glucose-4-epimerase, and 5.0 U of an enzyme having both activity of glucose-1-phosphate uridylyltransferase (EC 2.7.7.9) and activity of galactose-1-phosphate uridylyltransferase (EC 2.7.7.10), were added per milliliter of the solution, followed by 60 hours of reaction at 30° C. After 60 hours, the concentration of lacto-N-biose I in the reaction solution was 50 mM.

Example 11

Preparation of Lacto-N-Biose I Using Enzyme Having Both Activity of Glucose-1-Phosphate Uridylyltransferase (EC 2.7.7.9) and Activity of Galactose-1-Phosphate Uridylyltransferase (EC 2.7.7.10)

Lacto-N-biose I was synthesized as follows. The amount of the reaction solution was 1 milliliter. A substrate solution comprising 0.66 M sucrose, 0.60 M N-acetylglucosamine, 10 mM magnesium chloride, 30 mM phosphate buffer (pH 7.0), 1 mM UDP-glucose, and 1 mM sodium pyrophosphate at final concentrations was prepared. To the solution, 0.25 U of lacto-N-biose phosphorylase, 0.08 U of sucrose phosphorylase, 2.5 U of UDP-glucose-4-epimerase, and 5.0 U of an enzyme having both activity of glucose-1-phosphate uridylyltransferase (EC 2.7.7.9) and activity of galactose-1-phosphate uridylyltransferase (EC 2.7.7.10), were added per milliliter of the solution, followed by 60 hours of reaction at 30° C. After 60 hours, the concentration of lacto-N-biose I in the reaction solution was 50 mM in all cases.

INDUSTRIAL APPLICABILITY

According to the present invention, a method for producing lacto-N-biose I and galacto-N-biose inexpensively and conveniently is provided.

Effective use of lacto-N-biose I and galacto-N-biose that can be produced by the present invention is expected in relation to food additives, functional foods, or bulk or raw material ingredients for pharmaceutical preparations.

All publications, patents, and patent applications cited herein are incorporated herein by reference in their entirety.

The invention claimed is:

1. A method for producing lacto-N-biose I, wherein the method comprises causing:

(i) a combination of a carbohydrate raw material with an enzyme that catalyzes phosphorolysis of the carbohydrate raw material to give α-glucose-1-phosphate; and (ii) (a) an enzyme that converts α-glucose-1-phosphate and UDP-galactose to UDP-glucose and α-galactose-1-phosphate, respectively, with cofactor(s) and substrate(s) of said enzyme of (a); and/or (b) a combination of an enzyme that converts α-glucose-1-phosphate to UDP-glucose and an enzyme that converts UDP-galactose to α-galactose-1-phosphate with cofactor(s) and substrate(s) of said enzymes of (b); and/or (c) a combination of an enzyme having both activity of glucose-1-phosphate uridylyltransferase and activity of galactose-1-phosphate uridylyltransferase and cofactor(s) and substrate(s) of said enzyme of (c); to act in the presence of N-acetylglucosamine, phosphoric acid, lacto-N-biose phosphorylase (EC 2.4.1.211), 1,3-β-galactosyl-N-acetylhexosamine phosphorylase, and UDP-glucose-4-epimerase (EC 5.1.3.2), wherein lacto-N-biose I is obtained.

2. The method according to claim 1, wherein the combination of (i) is one combination or more selected from the group consisting of sucrose with sucrose phosphorylase (EC 2.4.1.7); starch or dextrin with phosphorylase (EC 2.4.1.1); cellobiose with cellobiose phosphorylase (EC 2.4.1.20); cellodextrin(s) with cellodextrin phosphorylase (EC 2.4.1.49) and cellobiose phosphorylase (EC 2.4.1.20); laminarioligosaccharide(s) with laminaribiose phosphorylase (EC 2.4.1.31) and/or β-1,3 oligoglucan phosphorylase (EC 2.4.1.30); and trehalose with trehalose phosphorylase (EC 2.4.1.231).

3. The method according to claim 1, wherein the enzyme of (a) is UDP-glucose-hexose-1-phosphate uridylyltransferase (EC 2.7.7.12), and cofactor(s) thereof, with UDP-glucose, UDP-galactose, or a mixture thereof; wherein the combination of (b) is selected from the group consisting of:
a combination of glucose-1-phosphate uridylyltransferase (EC 2.7.7.9), and cofactor(s) thereof, and galactose-1-phosphate uridylyltransferase (EC 2.7.7.10)), and cofactor(s) thereof, with UTP;
a combination of glucose-1-phosphate uridylyltransferase (EC 2.7.7.9), and cofactor(s) thereof, and galactose-1-phosphate uridylyltransferase (EC 2.7.7.10), and cofactor(s) thereof, with UDP-glucose and/or UDP-galactose and pyrophosphate; and
a combination of glucose-1-phosphate uridylyltransferase (EC 2.7.7.9), and cofactor(s) thereof, and galactose-1-phosphate uridylyltransferase (EC 2.7.7.10), and cofactor(s) thereof, with UTP and UDP-glucose and/or UDP-galactose and pyrophosphate; wherein
the combination of (c) is selected from the group consisting of the enzyme having both activity of glucose-1-phosphate uridylyltransferase and activity of galactose-1-phosphate uridylyltransferase, and cofactor(s) thereof, with UTP;
the enzyme having both activity of glucose-1-phosphate uridylyltransferase and activity of galactose-1-phosphate uridylyltransferase, and cofactor(s) thereof, with UDP-glucose and/or UDP-galactose and pyrophosphate; and
the enzyme having both activity of glucose-1-phosphate uridylyltransferase and activity of galactose-1-phosphate uridylyltransferase, and cofactor(s) thereof, with UTP and UDP-glucose and/or UDP-galactose and pyrophosphate.

4. The method according to claim 1, wherein one of said enzymes or more is/are immobilized on a carrier.

5. A method for producing galacto-N-biose, wherein the method comprises causing:
(i) a combination of a carbohydrate raw material with an enzyme that catalyzes phosphorolysis of the carbohydrate raw material to give α-glucose-1-phosphate; and
(ii) (a) an enzyme that converts α-glucose-1-phosphate and UDP-galactose to UDP-glucose and α-galactose-1-phosphate, respectively, with cofactor(s) and substrate(s) of said enzyme of (a); and/or (b) a combination of an enzyme that converts α-glucose-1-phosphate to UDP-glucose and an enzyme that converts UDP-galactose to α-galactose-1-phosphate with cofactor(s) and substrate(s) of said enzymes of (b); and/or (c) a combination of an enzyme having both activity of glucose-1-phosphate uridylyltransferase and activity of galactose-1-phosphate uridylyltransferase and cofactor(s) and substrate(s) of said enzyme of (c);
to act in the presence of N-acetylgalactosamine, phosphoric acid, lacto-N-biose phosphorylase (EC 2.4.1.211), and UDP-glucose-4-epimerase (EC 5.1.3.2), wherein galacto-N-biose is obtained.

6. The method according to claim 5, wherein the combination of
(i) is one combination or more selected from the group consisting of sucrose with sucrose phosphorylase (EC 2.4.1.7); starch or dextrin with phosphorylase (EC 2.4.1.1); cellobiose with cellobiose phosphorylase (EC 2.4.1.20); cellodextrin(s) with cellodextrin phosphorylase (EC 2.4.1.49) and cellobiose phosphorylase (EC 2.4.1.20); laminarioligosaccharide(s) with laminaribiose phosphorylase (EC 2.4.1.31) and/or β-1,3 oligoglucan phosphorylase (EC 2.4.1.30); and trehalose with trehalose phosphorylase (EC 2.4.1.231).

7. The method according to claim 5, wherein
the enzyme of (a) is UDP-glucose-hexose-1-phosphate uridylyltransferase (EC 2.7.7.12), and cofactors thereof, with UDP-glucose, UDP-galactose, or a mixture thereof; wherein
the combination of (b) is selected from the group consisting of:
a combination of glucose-1-phosphate uridylyltransferase (EC 2.7.7.9), and cofactor(s) thereof, and galactose-1-phosphate uridylyltransferase (EC 2.7.7.10), and cofactor(s) thereof, with UTP;
a combination of glucose-1-phosphate uridylyltransferase (EC 2.7.7.9), and cofactor(s) thereof, and galactose-1-phosphate uridylyltransferase (EC 2.7.7.10), and cofactor(s) thereof, with UDP-glucose and/or UDP-galactose and pyrophosphate; and
a combination of glucose-1-phosphate uridylyltransferase (EC 2.7.7.9), and cofactor(s) thereof, and galactose-1-phosphate uridylyltransferase (EC 2.7.7.10), and cofactor(s) thereof, with UTP and UDP-glucose and/or UDP-galactose and pyrophosphate; wherein
the combination of (c) is selected from the group consisting of the enzyme having both activity of glucose-1-phosphate uridylyltransferase and activity of galactose-1-phosphate uridylyltransferase, and cofactor(s) thereof, with UTP;
the enzyme having both activity of glucose-1-phosphate uridylyltransferase and activity of galactose-1-phosphate uridylyltransferase, and cofactor(s) thereof, with UDP-glucose and/or UDP-galactose and pyrophosphate; and
the enzyme having both activity of glucose-1-phosphate uridylyltransferase and activity of galactose-1-phosphate uridylyltransferase, and cofactor(s) thereof, with UTP and UDP-glucose and/or UDP-galactose and pyrophosphate.

8. The method according to claim 5, wherein one of said enzymes or more is/are immobilized on a carrier.

* * * * *